United States Patent
Desjobert et al.

(10) Patent No.: US 8,635,047 B2
(45) Date of Patent: Jan. 21, 2014

(54) METHOD OF INSPECTING POINT-OF-CARE BIOLOGICAL TEST APPLIANCES

(75) Inventors: Hélène Desjobert, Paris (FR); Jean Podvin, Beuvry la Foret (FR)

(73) Assignee: Accessible Conseils Sarl, Beuvry la Foret (FR)

( * ) Notice: Subject to any disclaimer, the term of this patent is extended or adjusted under 35 U.S.C. 154(b) by 972 days.

(21) Appl. No.: 12/312,852

(22) PCT Filed: Nov. 30, 2007

(86) PCT No.: PCT/FR2007/052430
§ 371 (c)(1),
(2), (4) Date: Feb. 9, 2010

(87) PCT Pub. No.: WO2008/065314
PCT Pub. Date: Jun. 5, 2008

(65) Prior Publication Data
US 2010/0131239 A1   May 27, 2010

(30) Foreign Application Priority Data
Dec. 1, 2006   (FR) ...................... 06 10529

(51) Int. Cl.
*G06F 11/30* (2006.01)
(52) U.S. Cl.
USPC ........................................................ 702/182
(58) Field of Classification Search
USPC ............... 702/31, 81, 83, 84, 85, 99, 104, 702/182–184
See application file for complete search history.

(56) References Cited

U.S. PATENT DOCUMENTS

| | | | |
|---|---|---|---|
| 5,835,384 A | 11/1998 | Lin | |
| 6,754,545 B2 * | 6/2004 | Haeuser et al. | 700/90 |
| 6,787,361 B1 | 9/2004 | Klee | |
| 7,521,244 B2 * | 4/2009 | Rannikko et al. | 436/15 |
| 2003/0154044 A1 * | 8/2003 | Lundstedt et al. | 702/104 |
| 2004/0078162 A1 | 4/2004 | Yundt-Pacheco | |
| 2004/0220761 A1 * | 11/2004 | Yundt-Pacheco | 702/84 |
| 2005/0177345 A1 | 8/2005 | Okuno et al. | |
| 2007/0083286 A1 * | 4/2007 | Kobayashi | 700/214 |

* cited by examiner

*Primary Examiner* — Manuel L Barbee
(74) *Attorney, Agent, or Firm* — Clark & Brody

(57) ABSTRACT

A method of inspecting point-of-care biological test appliances by means of an inspection appliance comprises the steps of: receiving qualitative data characterizing the test appliance and the environment in which the appliance is found; receiving the value of a control solution as measured by the test appliance; acquiring the value of the control solution as measured by a reference appliance; transmitting the test value, the reference value, and the qualitative data to a centralizing computer system; determining a bias expected between the received test value and the acquired reference value; comparing the test value with the reference value while taking the bias into account to obtain comparison data; storing the comparison data in association with the qualitative data; generating an inspection report within the computer system; and sending the report to the inspection appliance or to a computer terminal associated with the inspection appliance.

16 Claims, 2 Drawing Sheets

METHOD OF INSPECTING POINT-OF-CARE BIOLOGICAL TEST APPLIANCES

BACKGROUND OF THE INVENTION

The present invention relates to the general field of biological test appliances suitable for measuring or evaluating a biological variable at a point of care.

Such appliances are generally installed away from a laboratory, and frequently in an ambulatory service or even at a patient's home. Such appliances are generally portable, sometimes precalibrated, fast, and easy to use.

The invention applies more particularly to all point-of-care appliances for testing glycemia and it also applies to point-of-care testing of other biological parameters that can be measured by a biological test appliance at the point of care, i.e. away from a laboratory. Such parameters include blood gas, measuring hematocrits, measuring lactates, measuring urinary or blood ionograms, measuring urinary glucose, measuring uric acid, measuring cholesterol, measuring triglycerides, and any other physicochemical and/or biological parameter that is useful for diagnosis and decision making concerning the care to be given to a patient.

Depending on their construction, such point-of-care biological test appliances may operate continuously, or discretely.

The invention relates particularly to such point-of-care biological test appliances where it is useful or even essential to monitor their quality. Since such appliances are used in distinct places, sometimes on private premises, it is necessary to inspect that the values given by such appliances are correct.

At present, in order to inspect such a point-of-care biological test appliance, a measurement is performed by the appliance with the result of the measurement being sent to the laboratory, and simultaneously a venous blood sample is taken for sending to the laboratory as well as the measurement performed by the point-of-care biological test appliance.

A biologist then measures the biological value in the venous blood and compares the values that have been obtained in order to determine whether the point-of-care biological test appliance is functioning correctly or is functioning erroneously.

Insofar as point-of-care biological test appliances measuring glycemia generally use capillary blood, whereas the sample sent to the laboratory is venous blood, there is necessarily a bias between the values measured for those two types of blood.

This bias is made uncertain and is made greater by the fact that the test means are necessarily different and make use of different principles. Uncertainty concerning the real value of the bias gives rise to potential hazard if the point-of-care biological test appliance is declared valid when in fact the measurements it is making are significantly wrong. The inspection performed in that way can only be approximate and ultimately relies on the expertise of the biologist.

Nowadays another technique for inspecting a point-of-care biological test appliance exists and is recommended by the manufacturers of such appliances. Inspection is based on using a solution made available by the manufacturer for inspecting the point-of-care appliance.

Once the manufacturer has acquired a measurement for the solution, the value as measured is compared with ranges that are also supplied by the manufacturer.

This makes inspection direct, but it does not make it possible to evaluate the point-of-care biological test appliance relative to other appliances of other types and possibly operating on other principles.

It is also necessary to have a special control solution for each type of appliance in order to inspect all of the point-of-care biological test appliances in a group. That is difficult to implement and constitutes a source of error. It can therefore be harmful when several different types of point-of-care biological test appliance are in use by a given hospital service and when it is necessary to inspect their reliability and uniformity.

The invention thus proposes providing a method that supplements inspecting a point-of-care biological test appliance with the solution supplied by the manufacturer, and for this purpose the invention proposes an automatic technique that improves and simplifies inspection by performing measurements in parallel on the point-of-care biological test appliance and on a biological test appliance situated in a laboratory.

OBJECT AND SUMMARY OF THE INVENTION

An object of the present invention is thus to mitigate the drawbacks presented by the two presently-known methods by proposing a method of inspecting point-of-care biological test appliances for on-site implementation using an "inspection" appliance, the method comprising the steps of:

a) on-site inputting or reception of qualitative data characterizing a point-of-care biological test appliance for inspection and characterizing the environment in which the appliance is to be found;

b) on-site inputting or reception of the value of a biological variable of a "control" solution as measured by the point-of-care biological test appliance for inspection;

c) acquiring the value of the biological variable of the control solution as measured by a reference biological test appliance;

d) transmitting the input or received value, the acquired value, and the input or received qualitative data to a centralizing computer system;

e) within the centralizing computer system, determining a bias that is to be expected between the input or received value of the biological variable and the value as measured by the reference appliance, the expected bias being determined as a function of the input or received qualitative data, including data relating to the environment in which the appliance is used, and of comparison data stored in the computer system;

f) comparing the value as measured by the point-of-care biological test appliance with the value as measured by the reference appliance while taking the bias into account;

g) storing comparison data relating to the comparison performed in the computer system, said comparison data being stored in association with the qualitative data;

h) within the computer system, generating a inspection report; and i) sending the report to the inspection appliance or to a computer terminal associated with the inspection appliance.

Such a method makes it possible to automate inspecting the quality of point-of-care biological test appliances in the environments in which they are normally used with the help of an inspection appliance that is used for inspecting a plurality of point-of-care biological test appliances. The inspection appliance communicates with a centralizing computer system that is suitable for determining an appropriate bias, which bias might possibly differ for each inspection event.

In particular, the bias is determined in rational manner as a function of known qualitative data that is rationalized by inputting or receiving qualitative data encoded either in a numerical format or directly by the operator inputting codes, or by transforming the input from the operator into a numerical code.

The use of qualitative data qualifying the environment of the point-of-care biological test appliance for inspection also makes it possible to inspect point-of-care biological test appliances as a function of the environment in which they are used. The presence of such qualitative data also makes it possible, periodically, to inspect not only the state and the performance of point-of-care biological test appliances, but also the state of the consumables being used.

The method of the invention thus proposes making the use of point-of-care biological test appliances more secure by monitoring such equipment in a relatively continuous and uniform manner. It presents the advantage of making the results obtained by the point-of-care biological test appliances more uniform, or at least of providing elements for making comparisons between them. Knowledge of the bias that exists between the measurements made by appliances of different types is a major advantage since this makes it possible to take the bias directly into account when performing a comparison. The comparison then makes use directly of an expected target value as calculated from the bias and from the value measured on the reference appliance and received from the inspection appliance. According to the invention, the bias is determined and applied as a function of the situations observed and summarized in the qualitative data relating to the environment of point-of-care biological test appliance. This serves to make the operator's expertise more pertinent.

The expertise of the biologist then applies to defining all of the particular environmental and utilization conditions of any kind that may harm the quality of the results obtained in the particular context of use outside the laboratory.

The role of the biologist is to propose "questionnaires" organized to qualify these particular conditions of use in care establishments. These conditions are then compared with the initial recommendations of the manufacturers of the equipment used.

More generally, since the measurements performed by point-of-care biological test appliances are subject to inspection, the method serves to make more secure any medical acts that are performed as a function of such analyses.

Furthermore, the invention makes it possible to take account of the environment in which the point-of-care biological test appliance is used, and this can be very useful. The variability of the environment in which point-of-care tests are made can have so much influence on the results obtained as to make this practice dangerous. For example, a dirty glycemia reader can constitute a major vector for nosocomial infection, regardless of any potential disturbance to its results.

A detailed survey of the utilization environments in association with the differences in the results obtained from known solutions serves to enable a biologist:

- to continuously redefine the limits in which point-of-care biological test appliances should be used, including appliances that are used at home (home tests) or in doctors' surgeries (doctors tests) in the daily clinical practice of care establishments, or at any other utilization site; and
- to supplement user training or to take an appliance out of service, where appropriate, when the accurate observation of the circumstances of use of the equipment and the results obtained show that the limits of the method have been reached and that the level of risk is out of all proportion when the appliances are used outside the "secure" context of a medical test laboratory.

On receiving the report, the inspection appliance, assuming it is bidirectional, becomes a platform for monitoring the inspection process, all the way from inputting data to obtaining the result.

In other embodiments, the report is sent to a computer terminal, e.g. situated close to the inspection appliance or in premises, e.g. in a hospital, dedicated to centralized inspection of point-of-care biological test appliances. The computer terminal is associated with the inspection appliances in that it receives the reports relating to the point-of-care biological test appliances previously inspected by the inspection appliances.

In a preferred embodiment of the invention, the inspection appliance is a reference biological test appliance on which the value of the biological variable of the control solution is measured directly during the acquisition step.

With such a characteristic, the reference appliance that serves to perform the reference test for inspecting point-of-care biological test appliances also serves as an inspection appliance suitable for sending data to the centralizing system. Such an embodiment enables functions to be concentrated and combined within a single appliance.

According to another particular characteristic of the invention, the method includes a step of triggering a warning as a function of the content of the report received from the computer system.

Such a characteristic makes it possible to further automate inspection by giving the operator direct advice concerning the state of the point-of-care biological test appliance being inspected. The operator's own expertise then becomes a parameter that is of less importance than with prior art inspection methods. The report sent by the centralizing system then includes warning data which is subsequently interpreted by the inspection appliance or by the computer terminal that receives the report.

According to an advantageous characteristic, the comparison data associated with the qualitative data is stored in the form of a database.

Storing comparison data in association with qualitative data makes it possible to constitute a database that can be used subsequently for statistical evaluations or for subsequent determinations of a parameter, for example a bias that corresponds to some particular environmental situation.

In addition, organizing the data in the form of a database provides options concerning the traceability, the management, and the publication of data relating to inspecting point-of-care biological test appliances.

Several embodiments of the computer system can be envisaged.

It may be constituted by a single machine or by a plurality of machines interconnected by a network.

Thus, the method of the invention may operate in the form of a community of network services installed within a plurality of servers.

According to an advantageous characteristic, the method of the invention is suitable for operating in an initialization mode for the purpose of defining a bias for each point-of-care biological test appliance as a function of the control solution used, the bias being defined as being equal to the difference between the value of the variable as measured by the point-of-care biological test appliance and the value as measured by the reference appliance, or to the mean of said difference over a plurality of measurements performed by the point-of-care biological test appliance, with the bias being stored as part of the comparison data.

With such a characteristic, the comparison data then includes at least data concerning the bias that is to be expected as a function of the inspection situation, and thus as a function of the qualitative data, and of the point-of-care biological test appliance under consideration. Subsequent bias-determination steps make use of the stored comparison data. It should be observed at this point that the bias, which is defined for each appliance, may in fact be defined for each type of appliance and then attributed to all of the appliances of that type. It should also be observed that the bias, which may be a correction factor, is defined for each particular utilization situation of one or more appliances. To define biases, it is advantageous to make use of statistical analyses of the results in the database be peer group or by using any other type of criterion (method, appliance, etc.) that defines a particular situation.

In an implementation, the step of storing comparison data is performed only at the beginning of using and inspecting a point-of-care biological test appliance.

Such a characteristic enables the inspection method to be initialized progressively, in particular in terms of determining the bias. This amounts to a kind of training for the method that is to be used subsequently for later inspections.

Other means for defining biases can be implemented, in particular it is possible to define the expected target values and biases independently of the method of the invention before any use or inspection of the point-of-care biological test appliances and of the reference appliance. These target values and biases are then stored in the centralizing system before performing inspections. Naturally, the biases or correction factors and the target values need to be revised subsequently and regularly in order to avoid any drift and in order to detect any anomalies.

According to a particular characteristic of the invention, the qualitative data includes data qualifying the control solution.

The control solution may be selected from the following types of solution: a solution supplied by the manufacturer, the patient's blood, commercial total blood, or a so-called "universal" control solution. In this context, the term "universal" means that the measurement of the biological magnitude under test is substantially the same regardless of the biological test appliance used.

Such qualitative data makes it possible to define a bias for each control solution. Under such circumstances, during the bias-determination step, and when the "control solution" parameter is the only parameter used for determining the bias, the bias can be determined solely on the basis of knowledge of the qualitative data relating to the control solution. It will also be understood that the value of the bias will necessarily be different depending on the different control solutions that might be used. Incorporating data about the control solution within the qualitative data thus serves in particular to enable the bias to be determined more exactly.

Naturally, it can be envisaged that the parameter relating to the control solution is used in combination with other parameters involved in determining bias, for example the type of appliance, temperature, humidity, etc.

Depending on the application, the biological variable is selected from the following variables: glycemia, blood gas, hematocrit, lactates, urinary or blood ionogram, urinary glucose, creatinine, hemoglobin A1c, uric acid, cholesterol, triglycerides, or any other biological parameter, even if not known at present, providing point-of-care biological test appliances and an inspection appliance become available for performing the measurement.

The invention also provides an inspection appliance that can be used for implementing the method of the invention.

For this purpose, the inspection biological test appliance comprises:
means for inputting or receiving qualitative data characterizing a point-of-care biological test appliance for inspection and characterizing the environment in which the appliance is to be found;
means for inputting or receiving the value of a biological variable of a "control" solution as measured by the point-of-care biological test appliance for inspection;
means for acquiring the value of the biological variable of the control solution as measured by a reference biological test appliance; and
means for transmitting the input or received value, the measured value, and the input or received qualitative data to a centralizing computer system suitable for:
determining a bias that is to be expected between the input or received value of the biological variable and the value as measured by the reference appliance, the expected bias being determined as a function of the input or received qualitative data, including data reporting on the environment in which the appliance is used, and of comparison data stored in the computer system;
comparing the value as measured by the point-of-care biological test appliance with the value as measured by the reference appliance while taking the bias into account;
storing the comparison data relating to the comparison performed, said comparison data being stored in association with the qualitative data;
generating a inspection report; and
sending the report to the inspection appliance or to a computer terminal associated with said inspection appliance.

In a particular embodiment, the inspection biological test appliance further comprises means for receiving the inspection report.

According to another particular characteristic of the invention, the inspection biological test appliance further comprises warning means triggered as a function of the content of the report.

The invention also provides a centralizing computer system suitable for communicating with a plurality of inspection biological test appliances of the invention.

For this purpose, the centralizing computer system comprises:
means for receiving the value input to or received by the reference appliance, the value measured by a reference appliance, and the qualitative data transmitted by the inspection appliance;
means for determining a bias that is to be expected between the input or received value of the biological variable and the value measured by the reference appliance, the expected bias being determined as a function of the input qualitative data and of comparison data stored in the computer system;
means for comparing the value as measured by the point-of-care biological test appliance with the value as measured by the reference appliance while taking the bias into account;
storage means for storing comparison data relating to the comparison performed;
means for generating a inspection report; and
transmission means for sending the inspection report to the inspection appliance or to a computer terminal associated with said inspection appliance.

In a preferred implementation, the various steps of the method are determined by computer program instructions.

Consequently, the invention also provides a computer program on a data medium, the program being suitable for being implemented in an inspection appliance suitable for communicating with a centralizing computer system of the invention, the program including instructions adapted to implement the following steps:

inputting or receiving qualitative data characterizing a point-of-care biological test appliance for inspection;

inputting or receiving the value of a biological variable of a "control" solution as measured by the point-of-care biological test appliance for inspection;

acquiring the value of the biological variable of the control solution as measured by a reference biological test appliance; and transmitting the input value, the measured value, and input qualitative data to a centralizing computer system suitable for:

determining a bias that is to be expected between the value of the input biological variable as measured by the point-of-care biological test appliance and the value as measured by the reference appliance, the expected bias being determined as a function of the input qualitative data and of comparison data stored in the computer system;

comparing the value as measured by the point-of-care biological test appliance with the value as measured by the inspection appliance while taking the bias into account;

storing the comparison data relating to the comparison performed, said comparison data being stored in association with the qualitative data;

generating a inspection report; and sending the report to the inspection biological test appliance or to a computer terminal.

The invention also provides a computer program on a data medium, the program being suitable for being implemented in a centralizing computer system suitable for communicating with an inspection appliance of the invention, the program including instructions adapted to implement the following steps of:

receiving the input value, the measured value, and the qualitative data transmitted by the inspection appliance;

determining a bias that is to be expected between the input value of the biological variable after measurement by the point-of-care biological test appliance and the value as measured by the inspection appliance, the expected bias being determined as a function of the input qualitative data and of comparison data stored in the computer system;

comparing the value as measured by the point-of-care biological test appliance with the value as measured by the inspection appliance, while taking the bias into account;

storing comparison data relating to the comparison performed;

generating a inspection report; and transmitting the inspection report to the inspection biological test appliance or to a computer terminal.

These programs may make use of any programming language and may be in the form of source code, object code, or code intermediate between source code and object code, such as in a partially-compiled form, or in any other desirable form, e.g. in an html code.

The invention also provides a data medium readable by an inspection appliance or a computer system, and including instructions of a computer program as mentioned above.

The data medium may be any entity or device capable of storing the program. For example, the medium may comprise storage means such as a read-only memory (ROM), e.g. a compact disk read-only memory (CD ROM) or a microelectronic circuit ROM, or indeed magnetic recording means, e.g. a floppy disk or a hard disk, means for optical or magneto-optical recording, random access memory (RAM), Flash memory, or any other medium for conveying a stream or for storing data, whether digital or otherwise.

Furthermore, the data medium may be a transmission medium such as an electrical or optical signal, suitable for being conveyed via an electrical or optical cable, by radio, or by other means. The program of the invention may in particular be downloaded from a network of the Internet type.

Alternatively, the data medium may be an integrated circuit in which the program is incorporated, the circuit being adapted to execute or to be used in the execution of the method in question.

BRIEF DESCRIPTION OF THE DRAWINGS

Other characteristics and advantages of the present invention appear from the following description given with reference to the accompanying drawings that show an embodiment having no limiting character. In the figures.

DETAILED DESCRIPTION OF AN EMBODIMENT

Figure 1A:
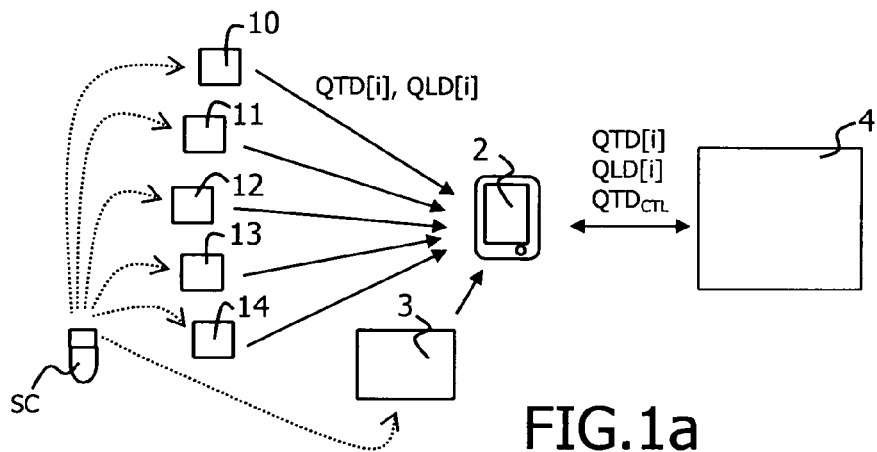
FIG. 1 is a diagram showing means for implementing a method of the invention.

FIG. 1a is a diagram showing the implementation of a method in a first embodiment of the invention for inspecting a group of point-of-care biological test appliances 10, 11, 12, 13, and 14. These appliances 10, 11, 12, 13, and 14 are suitable for measuring a biological magnitude and for giving a value of this magnitude. For example, below it is assumed that the appliances 10, 11, 12, 13, and 14 are appliances for measuring glycemia that are designed to be made available to patients, for example in a plurality of rooms in hospitals or medicalized homes.

Nevertheless, the invention is not restricted to appliances placed at a patient's bedside, in particular in a hospital. The invention also applies to ambulatory appliances in a patient's home or in any location outside a laboratory, in particular in emergency vehicles (ambulances), in the premises of dispensaries, clinics, doctors' surgeries, etc. In this context, terms frequently used are "home tests" and "doctors tests".

Nor is the invention is limited to appliances for measuring glycemia, but it covers any appliance outside the laboratory for measuring by any single technique or combination of techniques for chemical, physical, physicochemical, optical, electronic, computer, or automatic measurement, or for measurement by new methods for the purpose of performing biological testing.

In the method of the invention, a first glycemia measurement QTD[i] of a control solution SC is performed with each point-of-care biological test appliance i, for i=10, 11, 12, 13, or 14.

The control solution SC may be total blood obtained by being taken from a capillary or a vein, a proprietary solution from an appliance manufacturer, or indeed a solution developed specially for checking the reliability of point-of-care biological test appliances. In any event, the control solution SC needs to be identical throughout the method of inspecting the reliability of point-of-care biological test appliances. It is also known that the term "control solution" can in reality cover the use of a plurality of solutions, each presenting a different level of the variable being measured. Thus, it is possible to use three solutions at low, medium, and high levels as a "control solution" SC. The principle of the invention nevertheless remains identical. Under such circumstances, each quantitative measurement corresponds to a triplet of values.

The values QTD[i] as measured by each of the point-of-care biological test appliances may be input into a personal digital assistant (PDA) 2, constituting the inspection appliance in this embodiment. A "reference" biological test appliance 3 also measures the value of the biological variable. The reference appliance 3 may also be referred to as a comparison appliance. The inspection appliance 2 is then suitable for acquiring the value as measured by the reference appliance. This acquisition is advantageously performed by the measured value being input to or received by the PDA 2. The PDA 2 is also suitable for transmitting data to a centralizing system 4 via a computer terminal installed in the laboratory or the service in which the point-of-care biological test appliances are inspected. This transmission also includes qualitative data QLD[i] also input to the PDA 2. These steps are similar to those mentioned in the following outline description of the preferred embodiment.

Figure 1B:
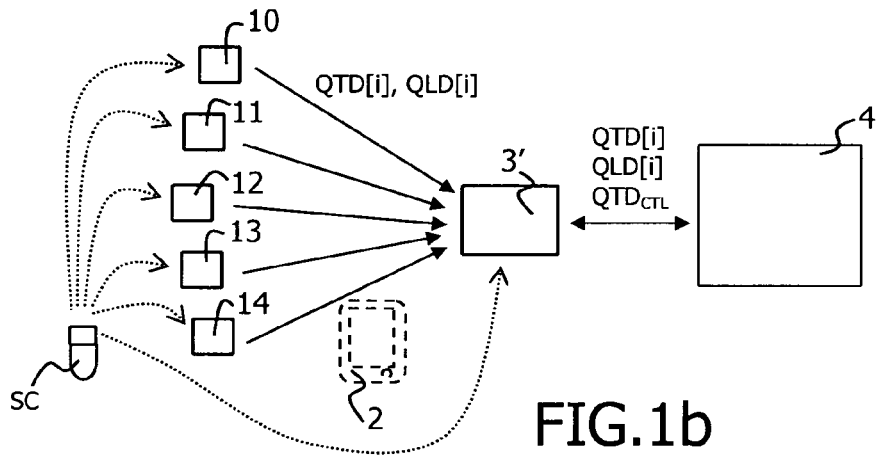

FIG. 1b is a diagram showing the implementation of a method in a preferred embodiment of the invention for inspecting a set of point-of-care biological test appliances 10, 11, 12, 13, and 14. These appliances 10, 11, 12, 13, and 14 are suitable for measuring a biological magnitude and for giving a value to said magnitude. By way of example, the appliances 10, 11, 12, 13, and 14 are appliances for measuring glycemia and they are designed to be made available to patients, e.g. in a plurality of rooms in hospitals or medicalized homes.

In the method of the invention, a first glycemia measurement QTD[i] is performed on a control solution SC by each point-of-care biological test appliance i, for i=10, 11, 12, 13, or 14.

Figure 2:
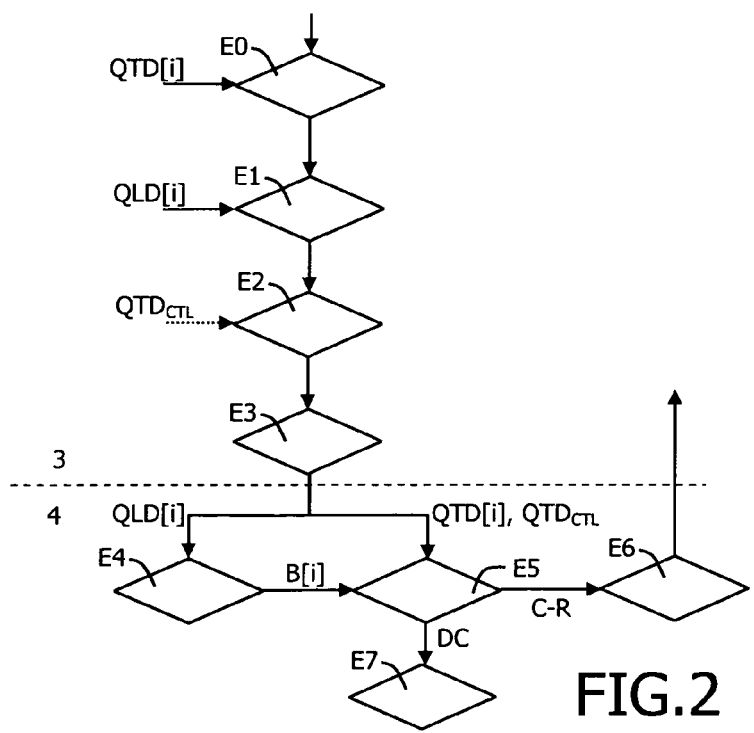
FIG. 2 is a diagrammatic flow chart of a method of the invention.

FIG. 2 is a diagrammatic representation of a method of the invention.

By way of example, the values QTD[i] measured by each of the point-of-care biological test appliance are input into a PDA 2 for subsequent transmission to an "inspection" biological test appliance 3' in a step E0. Such transmission can be performed with the help of a wired or wireless connection depending on the technology selected from those known for transferring data from one electronic appliance to another.

It is also possible to envisage implementing the invention without using a PDA 2, which is thus shown in dashed lines. Under such circumstances, the point-of-care biological test appliances i may themselves include means for directly transmitting the measured values QTD[i] to the inspection appliance 3'. The inspection appliance 3' may also have input means to enable data to be input directly, including the values QTD[i] as measured by the point-of-care biological test appliances i.

Figure 3:
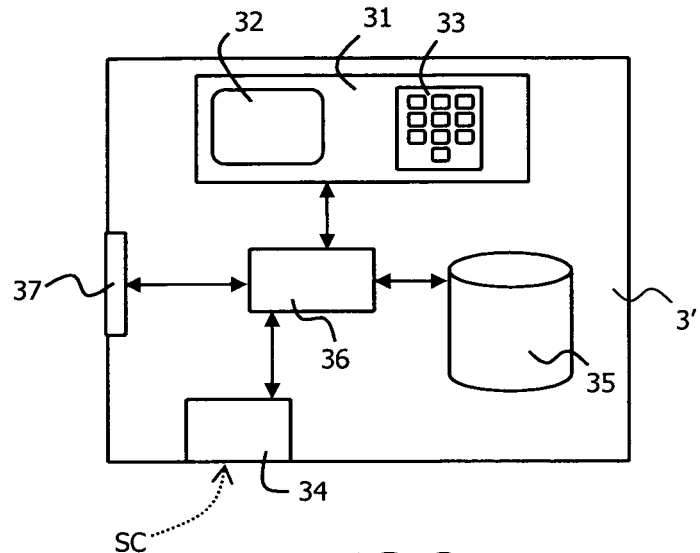
FIG. 3 is a diagram showing a inspection appliance of the invention.

FIG. 3 is a diagram of such an embodiment of a inspection appliance 3' of the invention. In this embodiment, the inspection appliance 3' includes a man-machine interface 31 including at least display means constituted by a screen 32 and input means constituted by a keypad 33.

Step E0 is thus a step of inputting or transmitting values for the biological variable as measured by the point-of-care biological test appliances i.

In the method of the invention, in a step E1, qualitative data QLD[i] is also provided before, after, or simultaneously with the transmission or the inputting of the values as measured on the point-of-care biological test appliances i. For this qualitative data, the same transmission or input means are used as are used for the quantitative data. The qualitative data QLD[i] identifies at least each of the point-of-care biological test appliances i for inspection. Thus, each value QTD[i] of the biological variable as input or transmitted is accompanied by at least one qualitative data item identifying the point-of-care biological test appliance i.

Examples of other types of qualitative data and of ways of encoding such data are given below.

Thereafter, in the preferred implementation, a step E2 is performed of measuring the value $QTD_{CTL}$ of the biological variable in the control solution SC by using the inspection appliance 3' which is specifically also the reference appliance.

For this purpose, and as shown diagrammatically in FIG. 3, the inspection appliance 3' includes measurement means 34. By way of example, these measurement means 34 operate on the basis of measurement reagent media, e.g. strips or wells on or in which a sample of the fluid for testing is deposited, here a sample of the control solution SC. The inspection appliance is thus constituted overall by measurement means, e.g. a photometer or an analyzer having analytic sensors, associated with a data input keypad.

The inspection appliance 3' then has the values QTD[i] as input or received corresponding to the measurements performed by the point-of-care biological test appliances, the measured value $QTD_{CTL}$ as measured by the inspection appliance, and also the qualitative data QLD[i] as input or received. By way of example, this data is stored in a memory 35 controlled by a microprocessor 36 within the inspection appliance 3' as shown in FIG. 3.

The inspection appliance 3' also has transmission and reception means 37 suitable for proceeding with a step E3 of transmitting data to a centralizing computer system 4. The system 4 may be implemented on a single machine or on a plurality of machines organized as a network. Communication between the inspection appliance 3' and the centralizing system 4 may be unidirectional or bidirectional.

Figure 4:
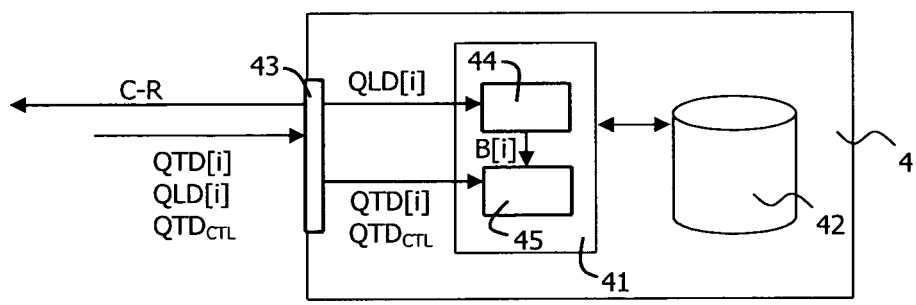
FIG. 4 is a diagram of a centralizing computer system.

As shown in FIG. 4, the computer system 4 comprises data transmission and reception means 43, data processor means 41, and received data storage means 42, at least. The storage means 42 are advantageously organized in the form of a database having fields that contain the qualitative data and that contain the quantitative data.

In an embodiment of the invention, the point-of-care biological test appliances are registered with the computer system 4 before performing any inspection. This registration may be performed automatically on the inspection appliance 3' suitable for performing the inspection requesting a subscription. The invention may thus be implemented in the form of a subscription to a network service that is accessible from inspection appliances, regardless of whether that appliance is the inspection appliance of the first embodiment or of the preferred embodiment. Either a local computer terminal to which the PDA 2 transmits the stored data, or the inspection appliance 3' itself therefore includes hardware and software means for communicating with the software means installed in the centralizing system 4 to which it is a subscriber. This subscription gives access to the database stored in the centralizing system 4.

The processor means 41 make use of the database to perform statistical processing on the qualitative and quantitative data received from the inspection appliance(s) 3'.

The centralizing computer system 4 may be in communication with a plurality of inspection appliances, e.g. situated in a plurality of services of a given hospital organization.

In particular, the data stored in the storage means 42 is used by the processor means 41 for evaluating the exactness of the measurements performed by the various point-of-care biological test appliances i.

This measurement accuracy is advantageously evaluated from the points of view of reproducibility and accuracy.

In order to inspect reproducibility, it is helpful to know a range of values within which the measured values QTD[i] are to be expected. This range, centered on a mean value, is typically defined with the help of a maximum departure from the mean ET[i].

Such a maximum departure from the mean ET[i] is generally a function of the type of point-of-care biological test appliance i that is in use and is common to all of the point-of-care biological test appliances of a given type.

In order to inspect accuracy, it is necessary also to know a possible bias B[i] that might exist between the value measured by each point-of-care biological test appliance i and the value $QTD_{cm}$ as measured by the inspection appliance 3'. The bias B[i] is a value that is expressed as an absolute value, and it is therefore positive. The bias B[i] may be added to or subtracted from the value $QTD_{CTL}$ measured on the inspection appliance 3'.

The term "bias" designates a numerical value or a mathematical function or a set of mathematical functions, that are calculated or described and that, when applied to the measured values, make it possible to write down a final inspection conclusion relating to the equipment being inspected.

This numerical value or this mathematical function or this set of mathematical functions, alone or in combination with one another, constitute a correction factor.

Such a correction factor serves in particular to enable a comparison to be made between a measurement made on total blood and a measurement made on plasma, or between a measurement of an element at one temperature and a measurement of an element at a different temperature, or under any other difference of environmental conditions such as humidity, atmospheric pressure, etc.

In any event, by taking account of the bias or the correction factor obtained by any appropriate method of calculation during the comparisons, it is possible to obtain a conclusion that is directly of use by the recipient of a inspection report without the recipient needing to take any account of a possible offset between measurements. In the meaning of the invention, the bias makes it possible to make two distinct data items comparable. Furthermore, the bias or correction factor can take account of a change of units between two data items.

The bias B[i] is advantageously defined as the difference between the true value VV of a sample and a single value QTD[i] or a mean of values QTD[i] as observed during a series of measurements on a single sample of the control solution. The true value VV may be defined absolutely when the solution comes from the manufacturer, or relatively as measured on the inspection appliance, or indeed on a laboratory appliance.

Under such circumstances, a bias is advantageously also defined for the inspection appliance by using the mean of the values $QTD_{CTL}$ obtained for a series of measurements.

In general, when the mean of the value QTD[i] is used, the bias can be expressed as a percentage using the following formula:

$$\text{bias in \%} = 100 * (\text{mean } QTD[i] - VV)/VV$$

It may also be calculated directly as a relative value:

$$\text{relative bias} = \text{mean } QTD[i] - VV$$

It should be observed at this point that these percentage and relative biases can have values that are negative. In fact, when the bias is defined as being the absolute value of the bias, this leads to the bias being subtracted from or added to the target value. Naturally, such subtraction or addition may be preceded by multiplication when the bias is expressed as a percentage. The target value may be the true value VV when defined by using the inspection appliance 3'.

The bias is advantageously redefined on each change of batch of reaction media, on each change of reagent, on each change of the control solution, on each calibration, and on each change of appliance or type of appliance.

Knowledge of such a bias B[i] then makes it possible to automate inspection of point-of-care biological test appliances i since the processor means 41 are then in a position to compare the values $QTD_{CTL}$ measured by the inspection appliance 3 and by each of the point-of-care biological test appliances i.

For example, it is then possible to detect calibration that is inexact, maintenance that is inappropriate, and the use of reagents that is erroneous, or indeed poor conservation of reagents, or wrong use, or wrong setting of the appliances.

If the operation of the point-of-care biological test appliance is satisfactory, then the measured values QTD[i] should always lie around a target value calculated with the help of the bias B[i] that may be expressed as a percentage or as a value for correcting a reference value. The width of the range in which the values lie around the target value is defined by the departure ET[i].

In addition to the fact that the biases B[i] change as a function of the point-of-care biological test appliance i being inspected, the observed biases B[i] can also vary as a function of the control solution used for inspecting the reliability of the point-of-care biological test appliances i, or indeed as a function of the conditions (temperature, environment, date of most recent calibration, . . . ) under which the point-of-care biological test appliances i and the inspection appliances 3 are used. Thus, the bias that is finally applied reflects either simulating a bias as defined between the reference appliance and the point-of-care biological test appliance with a local use environmental bias concerning utilization measured on site and forming part of the qualitative data, or simulating a bias as defined depending on the differences between the solution analyzed with the point-of-care biological test appliance and the reference appliance (e.g. capillarity blood from the patient, and plasma from the same patient as analyzed in a laboratory) with a local use environmental bias measured on site and forming part of the qualitative data. The bias may also be the result of a calculation making use of specific functions.

Knowledge of the existence of such a bias B[i] and determining the bias are elements that are crucial for using the point-of-care biological test appliances i concerned. It is also crucial to know variations in the bias as a function of qualitative data QLD[i] concerning the environment of the point-of-care biological test appliance i.

Figure 5:
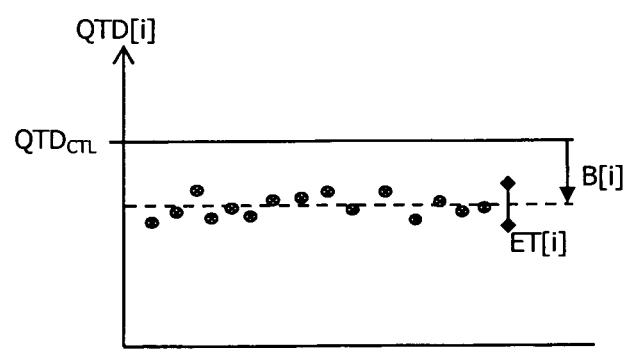
FIG. 5 is a diagram showing the presence of bias between measurements performed with point-of-care biological test appliances and the inspection appliance.

FIG. 5 shows the existence of bias B[i] between the measurements QTD[i] performed on a point-of-care biological test appliance i and the measurements $QTD_{CTL}$ performed on a inspection appliance 3. In order to ensure that the operation of the point-of-care biological test appliance can be declared correct, the measurements QTD[i] must lie within a range having the width of the departure ET[i] about a target value as obtained by subtracting the bias B[i] from the value $QTD_{CTL}$, or where appropriate, by applying the percentage corresponding to the bias to the value $QTD_{CTL}$.

The invention proposes rationalizing the presence of the bias B[i] and making this presence transparent to the user of the inspection appliance 3.

Until now, an operator inspecting a point-of-care biological test appliance i has generally made use of biases that are predefined and approximate. This is harmful to the accuracy of the inspection and possibly even to its reliability.

According to the invention, the bias B[i] is advantageously determined in an initialization step prior to implementing the method with a given control solution SC.

During initialization, at least two values QTD[i] and $QTD_{CTL}$ are measured for the control solution SC, one by means of the point-of-care biological test appliance i and the other by means of the inspection appliance 3.

These values are respectively input or received and acquired within the inspection appliance 3 or 3'. Qualitative data QLD[i] is associated with each value QTD[i] as input or received. The qualitative data QLD[i] includes at least data identifying the point-of-care biological test appliance i concerned by the bias B[i] constituting the subject matter of the initialization.

The bias B[i] is then defined for the point-of-care biological test appliance i within the centralizing system 4, as being the difference between the two values QTD[i] and $QTD_{CTL}$.

Once the bias B[i] has been defined, and using the maximum departure ET[i] from the mean that is known for the type of appliance constituted by the point-of-care biological test appliance i, a range is defined within which the measured values QTD[i] need to lie.

Advantageously, this initialization operation comprises repeating a certain number of measurements performed by the point-of-care biological test appliance i, and indeed a plurality of measurements performed by the inspection appliance 3.

Thus, the bias B[i] is defined as being the mean of the observed differences. The value of given to the bias B[i] is then more reliable and accurate.

Training concerning the value of the bias B[i] can also be performed over some initial number of inspections of each point-of-care biological test appliance i, when it is known that the appliance i is being used under good conditions.

Nevertheless, such training can impede detecting a problem that arises early with a point-of-care biological test appliance i. Drift in the value of the defined bias B[i] can then be observed but without aberrant measurements being reported.

Once the bias B[i] has been defined within the processor means 41 for each of the point-of-care biological test appliances i, and where appropriate for distinct qualitative data items, each time data is received from one of the point-of-care biological test appliances i, it is necessary to determine the bias B[i] as a function of the corresponding qualitative data.

In order to perform such a step E4 of determining the bias B[i], the processor means 41 make use of means 44 for determining a bias B[i] for each point-of-care biological test appliance i.

In step E4, the means 44 for determining the bias B[i] determines the bias, at least as a function of qualitative data QTD[i], in particular as a function of the data identifying the point-of-care biological test appliance i being inspected.

In the invention, it is also envisaged that the means 44 for determining the bias B[i] that are included in the processor means 41 should be capable of applying a relationship for variation in the bias B[i] as a function of the temperature or of other qualitative data QLD[i] concerning the environment, for example humidity or atmospheric pressure. Under such circumstances, when the qualitative data relating to the environment of the point-of-care biological test appliance reports that temperatures are too high (or, for example, humidity or atmospheric pressure are too high or too low), provision can be made to ensure that no bias is delivered and that a warning signal is returned in the report concerning the use of the point-of-care biological test appliance.

Under such circumstances, the qualitative data QLD[i] advantageously includes data concerning the temperature, the humidity, or the atmospheric pressure, for example, at which the point-of-care biological test appliance i is being used. The qualitative data QLD[i] thus includes meteorological data, i.e. data that can be quantified. The term "qualitative" is applied thereto so as to distinguish such data from the "quantitative" data that designates biological test measurements performed by the appliance.

In the absence of such data, a predefined reference temperature is used for determining the bias B[i].

Thereafter, in a comparison step E5, the measured value QTD[i] as transmitted to the inspection appliance 3 and then to the centralizing system 4 is compared with the value $QTD_{CTL}$ as measured by the inspection appliance 3, while taking account of the bias B[i] as determined in step E4, before making the comparison.

This comparison step E5 is performed by comparator means 45. Within the processor means 41, comparison causes a report C-R to be created and transmitted in a step E6 to the inspection appliance 3, which receives it over the transmission and reception means 37 when the inspection appliance 3 is bidirectional, or from a device associated with said inspection appliance 3. This associated device may be a computer terminal or any terminal for receiving information and associated with the addressee, such as a fax, etc., situated on the same premises as the inspection appliance 3 or nearby or in the hospital service performing the inspections.

The report C-R reproduces at least some of the qualitative data and highlights pertinent results. These pertinent results may be summarized by simple mentions such as "good", "check", "change", depending on the departure of the measured value from a value that is to be expected when the bias B[i] is taken into account. When it is necessary to check the point-of-care biological test appliance i, a measurement performed by said point-of-care biological test appliance i can then still be compared with a measurement performed on venous blood as an emergency in a laboratory and submitted to the expertise of a biologist.

By way of example, the report contains the date, the identity of the point-of-care biological test appliance or "reader", the code specifying the service in which the appliance is installed, frequency of use, reader state, the regularity or otherwise of a weekly inspection, the state of the control solution, the presence or absence of a brochure concerning the procedure for using the point-of-care biological test appliance, the batch number of the reagent strip used, the state of the strip, the quality of reader calibration, and the percentage of the departure from the target value. The report may also include information concerning the lifetime of the electrode, and the presence of the calibration electrode. The percentage departure is used directly to decide whether the appliance is good for use, in need of verification, or needs to be changed.

Comparison also gives rise to a step E7 of storing the comparison data DC, which data comprises, for example, the difference between the values QTD[i] measured by the point-of-care biological test appliance i and the value $QTD_{cm}$ measured by the inspection appliance 3 when the bias B[i] is determined by training during the initial inspections of a point-of-care biological test appliance i.

The comparison data DC then constitutes a database that can be used to provide overall monitoring of a group of point-of-care biological test appliances, including statistical monitoring of the problems observed.

Nevertheless, the bias may also be defined before any inspection and without any initialization of the method. Under such circumstances, values for the bias, the departures, and other inspection parameters are defined without making use of any inspection appliance, and they are input into the centralizing system for subsequent use. Prior laboratory measurements together with statistical calculations can serve in particular for this purpose for each of the control solutions envisaged. The comparison data DC is coupled with the various items of qualitative data QLD[i] in order to determine which qualitative parameters have an influence on the operation and the state of the point-of-care biological test appliances i.

The stored data can also be used as an archive base.

By using such an archive base, it is possible to inspect point-of-care biological test appliances while using a patient's blood. Under such circumstances, the archive base is used to determine statistically what bias ought to be expected as a function of the input qualitative data. The bias is then determined in particular as a function of the characteristics concerning the patient and included in the qualitative data.

The qualitative data then advantageously includes the age of the patient. For example, the bias observed for the blood of a newborn under the same environmental conditions can be used for inspecting a point-of-care biological test appliance with the help of blood from a newborn.

Information about the type of service (in particular neonatal) can also be used so that an average of the expected bias can be determined as a function of the age, at least approximate, of the patient.

The bias may also be determined as a function of high or low contents of the measured components. The use of the database is then found highly appropriate and very useful.

In addition, since the database is usually located remote from health premises, or at least in dedicated premises, it presents guarantees of anonymity and security concerning the exactness of the data.

The qualitative data can also provide information about hemoconcentration or hemodilution.

The qualitative data may comprise descriptions of substances used and the environment in which the point-of-care biological test appliance is used.

The qualitative data advantageously includes information concerning the type of the point-of-care biological test appliance, the state of the appliance, appliance maintenance, its method of use, its location, its serial number, its frequency of use, and calibration. The data may also advantageously include time stamps. The identification data may be input or detected automatically by a PDA or directly via the inspection appliance.

The qualitative data is advantageously input using digital coding. It is then obtained with the help of a sequential questionnaire associating each data item concerning the environment in which the point-of-care biological test appliance being inspected is used with a code, e.g. a number, for each state of each data item.

In the qualitative data as input in this way, there is data that is of use in making the report and in performing statistical studies concerning the operation of the point-of-care biological test appliances.

By way of example, the qualitative data may be encoded on 20 digits as follows:

1. Service code (two digits selected from a list).
2. Serial number of the reader (three digits selected from a list of reader equipment numbers.
3. Frequency of use (one digit):
    0: less than once per day
    1: one to four times per day
    2: four to 20 times per day
    3: more than 20 times per day
    4: reserved, patient room
    9: isolation room
4. General state of reader (one digit):
    0: general state good
    1: reader dirty
    2: reader damaged
    3: reader out of operation
    4: reader damaged—to be changed
    9: appliance inaccessible
5. Weekly inspection performed by nursing staff (one digit):
    0: regular
    1: irregular
    3: sheet not available
    4: never
    9: not checked
6. Control solutions (one digit):
    0: satisfactory
    1: expiry date in current month
    2: solution expired
    3: solution missing
    4: opening date not specified
    5: use>3 months (change)
    9: not checked
7. Presence of the instruction (one digit):
    0: manual available
    1: manual not available
    2: no manual
    9: not checked
8. Reagent strip batch number (six digits: batch number on the back of the strip)
9. State of strip storage (one digit):
    0: good
    1: no strip
    2: more than one batch in use
    3: strips not authorized
    9: not checked
10. Strip expiration date (one digit):
    0: data not exceeded
    1: data in current month
    2: date exceeded
    3: no strips
    9: not checked
11. Calibration electrode (one digit):
    0: present
    1: absent
    2: incompatible
    3: needs renewing
    9: not checked
12. Reader calibration (one digit indicating whether the reagent strip batch number corresponds to the reader calibration code):
    0: satisfactory
    1: not satisfactory
    2: erroneous
    3: needs to be redone
    9: not checked Advantageously, input of the value measured by the point-of-care biological test appliance is also encoded in this input sequence in the form of a thirteenth code heading:

13. Result of reader inspection (X digits, e.g. X=3): give the result QTD[i] of the inspection as displayed on reader i in the form of X digits (e.g.: 045 for 04.5 millimoles per liter (mmol/L).

By using these associated items of qualitative and quantitative data, the invention enables the performance of point-of-care biological test appliances to be evaluated while taking account of the context in which they are used.

In the invention, the qualitative data is assessed with the help of a questionnaire of the kind described above. The questionnaire may be created and varied by users themselves. Each of the answers can likewise be varied. In particular, each recorded element may optionally be given a score enabling each answer to be assessed automatically. The data generated by the inspection comprises items of different kinds, qualitative or quantitative, but both kinds can be given a score.

The table below gives an example of a questionnaire with two questions, each having a set of answers characterized by a score. This example relates to inspecting a Medisense OPTIUM capillary glycemia reader and the scores are allocated on the basis of each answer to a multiple-choice questionnaire.

Each questionnaire that has been filled in has a choice of answers and thus an accumulated score that can be used for characterizing an entire observation providing the scores are well chosen. Here a maximum of 0 immediately indicates good quality, whereas a score that is not 0 gives an idea about the magnitude of problems.

Advantageously, each score for each answer can be used as a relationship or a classifier or for searching in history or archive mode.

Each score is included in an overall score enabling a rapid validation system to be provided.

| Questions | | | |
|---|---|---|---|
| Order | Question | Score | Type |
| 1 | Temperature | | Multiple choices |
| | 18° C.-20° C. | 0 | |
| | 20° C.-22° C. | 0 | |
| | 22° C.-24° C. | 0 | |
| | 24° C.-26° C. | 1 | |
| | 26° C.-28° C. | 2 | |
| | 28° C.-30° C. | 3 | |
| | Greater than 30° C.: WARNING | 4 | |
| | Less than 18° C.: WARNING | 5 | |
| 2 | Humidity | | Multiple choices |
| | 10% to 15%: WARNING | 2 | |
| | 15% to 20%: WARNING | 1 | |
| | 20% to 30% | 0 | |
| | 30% to 50% | 0 | |
| | 50% to 60% | 0 | |
| | 60% to 70%: WARNING | 3 | |
| | Greater than 80%: WARNING | 4 | |
| | Less than 10%: WARNING | 5 | |

For each question in the multiple choice questionnaire, the user sees a plurality of windows or boxes for checking. When the answer to the question can be either selected from a certain number of options (multiple choice) or may be given freely, those two options are advantageously made available to the user in the form of a check box: either "multiple choice" or "free-response field".

The user then selects one of the multiple choice items or inputs a free response in a window displayed for this purpose on the screen of the inspection appliance or on the terminal associated with the inspection appliance.

The score that corresponds to the input or the selected item is then advantageously displayed in an adjacent window. It is also possible to display only a total score taking account of the input or of the item chosen.

In the example given above concerning temperature, in the range 18° C. to 24° C., the appliance is in normal operating conditions so the score is zero. The score increases as the observed temperature rises to reach scores of 4 or 5 at which warnings are triggered.

For humidity, in the range 20% to 60%, the operation of the inspection appliance is expected to be normal. Outside these conditions, proper operation is threatened and warnings are triggered as soon as a score of 2 is reached.

A parameter window is advantageously made available to the user so that on each question the user associates a score with each range of values, and at a given score, an optional warning.

Such a parameter window enables each user to select the limits within which environmental conditions are acceptable.

The score associated with each question can give rise to a warning and can consequently lead to an appliance being overhauled or removed.

In addition, an overall score is advantageously calculated. It is cumulative and may for example be the sum of the individual scores of the questions.

A zero score indicates that the appliance is in ideal operating conditions. The appliance can then be validated quickly.

A small but non-zero score, e.g. a score of 2, because the observed temperature is too high, indicates that operating conditions are acceptable. It is then possible to validate use of the appliance quickly.

When a higher score is observed, e.g. 7, then there is a problem that needs investigating. It is then recommended to perform validation using in-depth inspections.

Finally, for a score that is greater than 10, e.g. 12, it is necessary to perform in-depth validation of the appliance.

The questionnaire advantageously includes a question concerning appliance maintenance. Under such circumstances, a report that the appliance is dirty, using a dedicated window, will be associated with a score of 10 so that a warning is necessarily triggered.

With the invention, it is possible to provide the user with a table comprising a list of point-of-care biological test appliances for inspecting together with a score as associated with each of the appliances.

The operator in charge of inspecting point-of-care biological test appliances then need only look down the score column to identify which appliance(s) is/are a problem.

The scores may also be presented in the form of a set of points spread along an abscissa axis, with the associated scores being plotted up the ordinate axis. It is shown below that such a presentation is particularly suitable for inspecting the exactness of measurements performed by the appliance.

Thus, an overall score for each assessment enables a data set to be validated quickly, automatically, and in full.

As explained above, on the topic of qualitative data, each biologist can build up questionnaires for collecting optionally numerical data relating to the environment and to the security of use of point-of-care biology equipment.

Each question comprises a selection of answers, each of which is associated with a score, which itself may optionally be associated with one or more colors, selected as desired by each biologist and depending on the intuitive nature of the information given. For example, each answer may be associated with a score and with a color representing the importance of the answer: green=OK, orange=take care, red=warning. Once a question is associated with the color red, that tells the biologist directly that the appliance must not be used, so the biologist must take the appropriate action.

Each questionnaire, and thus each suite of questions presents an overall score associated with one or more colors representing the various answers selected during the assessment.

Each questionnaire filled in at the inspection site records the various answers and this data is transmitted by computer connection to the database. The database takes note of the results and may in particular express them in the form of a detailed score or an overall score.

The overall score using one or more colors enables the data derived from the inspection to be presented in a manner that is visual, intuitive, and fast, enabling the biologist or the technician to decide almost immediately whether the assessment requires rapid validation, e.g. including printing and/or sending the report immediately, or in-depth validation, including verification of the data as input, of its interpretation, and of the conclusions drawn prior to printing out the report.

The detailed score with or without color enables the various answers to a given questionnaire to be analyzed statistically and also makes it possible to provide high-performance and detailed retrospective analysis of accumulated qualitative data.

On the topic of qualitative data, the results obtained are compared with value ranges suitable, for example, for deciding between the following items: accept the values obtained; inspect the equipment again; refuse/exclude the equipment. The results obtained can also be compared with target values, e.g. after calculating a departure or calculating an index.

These comparisons lead to a conclusion that may be given a score optionally associated with one or more colors: conclusion 1: score 1, conclusion 2: score 2, conclusion n: score n, . . . . The score, optionally together with color, can be processed in a manner identical to the processing of qualitative data.

The score is then advantageously zero when the measurement complies with the bias that is associated with the point-of-care biological test appliance. It is higher to a greater or lesser extent depending on the value of the departure observed for a given appliance.

These scores are advantageously presented in the form of a set of points spread along an abscissa axis, with the associated scores being plotted up the ordinate axis. On such a graph, the acceptable departure zone can be in gray and the non-acceptable departure zone can be pink with an intermediate zone that is yellow.

When the score, representative of the departure, goes beyond the previously-defined value range, it can be seen at a glance which appliances present exactness that lies outside an acceptable departure range. By displaying an identifier for the appliance in question close to each of the points, it is possible to validate the exactness of the appliance very quickly.

This thus provides an overall system for processing qualitative and quantitative data for ensuring the quality of tests performed by point-of-care biological test appliances independently of the graphical systems commonly used in statistics.

It is also known that the health warnings issued by the appropriate authorities, including AFSSAPS in France, seek to discover what equipment and consumables, if any, are present at a site of use and as a function of trademark, model, serial number, batch number, reference, expiration date, fabrication date, or any other mode of identification, including bar codes, etc., often for the purpose of removing them to stop them being used.

The invention enables the equipment in use to be monitored by coding qualitative data relating to the operation and the use of the appliance. In one of its applications, the invention thus makes it possible to pass such warnings quickly into the field. Furthermore, this can be done automatically by appropriately setting the way the score is calculated so that using a given piece of equipment that is the subject of a health warning, e.g. using a batch of defective consumables with a given point-of-care biological test appliance, gives rise to a score that means that the appliance should no longer be used.

This application of the invention enables patient care to be made very secure, in particular when supplier laboratories withdraw equipment because of an anomaly.

This constitutes top-down information relying on the traceability made possible by the invention.

One of the major innovative characteristics of the invention is that it enables the validation of one or more appliances being inspected to be accelerated and it enables qualitative data to be processed statistically. In addition, the invention enables assessments to be performed at the site of the inspection, thus making the conditions of use of the equipment secure.

In particular, the invention makes it possible to validate quality assurance data quickly for point-of-care biological test appliances by making it possible to analyze the qualitative and quantitative data obtained by assessments performed on the actual site where the point-of-care biological test appliance is being used.

Application of the invention makes it possible to satisfy the requirements of ISO standard 22870: 2006 Point-of-care testing (POCT)—requirements for quality and competence" specific to point-of-care biological test appliances which are particular appliances for which problems arise that are distinct from those encountered with laboratory appliances.

Advantageously, the inspection appliance 3 includes means for managing one or more subscriptions to the database and data processing service offered by the centralizing computer system 4. Managing such a subscription makes use of means known to the person skilled in the art for managing a subscription to a network service, e.g. on the Internet.

The means provided by the invention make it possible to compare the results of measurements obtained in particular contexts with the help of a database, from which it is possible to enlarge the test data, or on the contrary to select particular test data. Such comparisons make it possible to reach a conclusion about the state of point-of-care biological test appliances, and to comment on and document such conclusions. The conclusions are reached quickly and therefore enable point-of-care biological test appliances to be diagnosed early.

Finally, it should be observed that various implementations can be provided on the principles of the invention. In particular, the detection means may be physically integrated in the sensor, as shown in FIG. 1, or they may be associated therewith, as shown in FIG. 4.

The invention claimed is:

1. A method of inspecting point-of-care biological test appliances for on-site implementation using an inspection appliance, the method comprising the steps of:
   a) on-site inputting or reception of qualitative data (QLD[i]) characterizing a point-of-care biological test appliance for inspection and characterizing the environment in which the appliance is to be found;
   b) on-site inputting or reception of a value (QTD[i]) of a biological variable of a control solution as measured by the point-of-care biological test appliance for inspection;

c) acquiring a value ($OTD_{CTL}$) of the biological variable of the control solution as measured by a reference biological test appliance;

d) transmitting the input or received value (QTD[i]), the acquired value ($QTD_{CTL}$), and the input or received qualitative data (QLD[i]) to a centralizing computer system;

e) within the centralizing computer system, determining a bias that is to be expected between the input or received value (QTD[i]) of the biological variable and the value ($QTD_{CTL}$) as measured by the reference appliance, the expected bias being determined as a function of the input or received qualitative data (QLD[i]), including data relating to the environment in which the appliance is used, and of comparison data stored in the computer system;

f) comparing the value (QTD[i]) as measured by the point-of-care biological test appliance with the value ($QTD_{CTL}$) as measured by the reference appliance while taking the bias into account;

g) storing comparison data relating to the comparison performed in the computer system, said comparison data being stored in association with the qualitative data;

h) within the computer system, generating a inspection report; and i) sending the report to the inspection appliance or to a computer terminal associated with the inspection appliance.

2. A method of according to claim 1, wherein step (c) is performed directly by the inspection appliance as a reference biological test appliance.

3. A method according to claim 1, wherein it includes a step of triggering a warning as a function of the content of the report received from the computer system.

4. A method according to claim 1, wherein the comparison data associated with the qualitative data is stored in the form of a database.

5. A method according to claim 1, wherein the computer system is constituted by a single machine or by a plurality of machines connected together by a network.

6. A method according to claim 1, wherein it is suitable for operating in an initialization mode for the purpose of defining a bias for each point-of-care biological test appliance as a function of the control solution used, the bias being defined as being equal to the difference between the value (QTD[i]) of the variable as measured by the point-of-care biological test appliance and the value ($QTD_{CTL}$) as measured by the reference appliance, or to the mean of said difference over a plurality of measurements performed by the point-of-care biological test appliance, with the bias being stored as part of the comparison data.

7. A method according to claim 1, wherein the step of storing comparison data is performed only at the beginning of using and inspecting a point-of-care biological test appliance.

8. A method according to claim 1, wherein the qualitative data (QLD[i]) include data qualifying the control solution.

9. A method according to claim 1, wherein the biological variable is selected from the following variables: glycemia, blood gas, hematocrit, lactates, urinary or blood ionogram, urinary glucose, creatinine, hemoglobin A1c, uric acid, cholesterol, triglycerides.

10. A method according to claim 1, wherein a score is associated with each reported qualitative data item, and in that a score is associated with each quantitative data item as a function of the comparison step, and in that a final score obtained by summing or performing a calculation on the qualitative and quantitative data scores constitutes one of the elements of the report or serves to enable a warning step to be triggered or not triggered.

11. A method according to claim 10, wherein it includes a step of automatically associating predefined colors with each score, the colors enabling scores that are high, at the limit, or abnormal to be characterized instantly, and enabling each score to be processed specifically depending on its relative importance.

12. An inspection appliance from which a method according to claim 1 is implemented on site, the appliance comprising:
   means for inputting or receiving qualitative data (QLD[i]) characterizing a point-of-care biological test appliance for inspection and characterizing the environment in which the appliance is to be found;
   means for inputting or receiving a value (QTD[i]) of a biological variable of a control solution as measured by the point-of-care biological test appliance for inspection;
   means for acquiring a value ($QTD_{CTL}$) of the biological variable of the control solution as measured by a reference biological test appliance; and
   means for transmitting the input or received value (QTD[i]), the measured value ($QTD_{CTL}$), and the input or received qualitative data (QLD[i]) to a centralizing computer system (4) suitable for:
      determining a bias that is to be expected between the input or received value (QTD[i]) of the biological variable and the value ($QTD_{CTL}$) as measured by the reference appliance, the expected bias being determined as a function of the input or received qualitative data (QLD[i]), including data reporting on the environment in which the appliance is used, and of comparison data stored in the computer system;
      comparing the value (QTD[i]) as measured by the point-of-care biological test appliance with the value ($QTD_{CTL}$) as measured by the reference appliance while taking the bias (B[i]) into account;
      storing the comparison data relating to the comparison performed, said comparison data being stored in association with the qualitative data (QLD[i]);
      generating a inspection report; and
      sending the report to the inspection appliance or to a computer terminal associated with said inspection appliance.

13. An inspection appliance according to claim 12, wherein it includes means for measuring the value ($QTD_{CTL}$) of the biological variable of the control solution, and in that it constitutes the reference biological test appliance.

14. An inspection biological test appliance according to claim 12, wherein it further comprises means for receiving the inspection report.

15. An inspection biological test appliance according to claim 14, wherein it further comprises warning means triggered as a function of the content of the report.

16. A centralizing computer system suitable for communicating with a plurality of control biological test appliances according to claim 12, the computer system comprising:
   means for receiving the value (QTD[i]) input to or received by the reference appliance, the value ($QTD_{CTL}$) measured by a reference appliance, and the qualitative data (QTD[i]) transmitted by the inspection appliance;
   means for determining a bias that is to be expected between the input or received value (QTD[i]) of the biological variable and the value ($QTD_{CTL}$) as measured by the reference appliance, the expected bias being determined as a function of the input qualitative data (QLD[i]) and of comparison data stored in the computer system;

means for comparing the value (QTD[i]) as measured by the point-of-care biological test appliance with the value ($QTD_{CTL}$) as measured by the reference appliance while taking the bias into account;

storage means for storing comparison data relating to the comparison performed;

means for generating a inspection report; and transmission means for sending the inspection report to the inspection appliance or to a computer terminal associated with said inspection appliance.

\* \* \* \* \*

UNITED STATES PATENT AND TRADEMARK OFFICE
CERTIFICATE OF CORRECTION

PATENT NO. : 8,635,047 B2  
APPLICATION NO. : 12/312852  
DATED : January 21, 2014  
INVENTOR(S) : Desjobert et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1224 days.

Signed and Sealed this
Twenty-second Day of September, 2015

Michelle K. Lee
*Director of the United States Patent and Trademark Office*